(12) United States Patent
Strutt et al.

(10) Patent No.: US 11,596,541 B2
(45) Date of Patent: Mar. 7, 2023

(54) CONDOMS

(71) Applicant: Cambridge Design Partnership LLP, Cambridge (GB)

(72) Inventors: Benjamin John Strutt, Cambridge (GB); Aki Hannu Einari Laakso, Cambridge (GB); Michael James Worth, Cambridge (GB)

(73) Assignee: Cambridge Design Partnership LLP, Cambridge (GB)

( * ) Notice: Subject to any disclaimer, the term of this patent is extended or adjusted under 35 U.S.C. 154(b) by 156 days.

(21) Appl. No.: 16/340,080

(22) PCT Filed: Oct. 6, 2017

(86) PCT No.: PCT/GB2017/053039
§ 371 (c)(1),
(2) Date: Apr. 5, 2019

(87) PCT Pub. No.: WO2018/065790
PCT Pub. Date: Apr. 12, 2018

(65) Prior Publication Data
US 2020/0054479 A1 Feb. 20, 2020

(30) Foreign Application Priority Data
Oct. 7, 2016 (GB) ...................... 1617063

(51) Int. Cl.
*A61F 6/04* (2006.01)
(52) U.S. Cl.
CPC .......... *A61F 6/04* (2013.01); *A61F 2006/047* (2013.01)

(58) Field of Classification Search
CPC ............ A61F 6/18; A61F 6/144; A61F 6/148; A61F 6/142; A61F 6/02; A61F 6/04;
(Continued)

(56) References Cited

U.S. PATENT DOCUMENTS 2,586,674 A 11/1949 Lonne
4,798,600 A 1/1989 Meadows
(Continued)

FOREIGN PATENT DOCUMENTS

AU 5719796 9/1997
AU 5700096 10/1997
(Continued)

OTHER PUBLICATIONS

International Searching Authority, International Search Report and Written Opinion, issued for PCT/GB2017/053039, dated Apr. 13, 2018 (12 pages).

*Primary Examiner* — Ophelia A Hawthorne
(74) *Attorney, Agent, or Firm* — Polsinelli PC; Gregory P. Durbin

(57) ABSTRACT

A condom comprising a continuous elastic tubular wall with a closed distal end and an open proximal end and further improving features. In one embodiment the condom further comprises a teat at the closed distal end, wherein the teat comprises a neck and a head, and wherein in use, the teat is retained partially or fully inside of the continuous elastic tubular wall, and the teat forms a chamber that is tillable with a fluid or phase change formulation which is released externally in use.

23 Claims, 14 Drawing Sheets

(58) Field of Classification Search
CPC .. A61F 2006/043; A61F 13/471; A61F 6/005; A61F 2006/048; A61F 5/41; A61F 2006/047; A61B 5/06
See application file for complete search history.

(56) References Cited

U.S. PATENT DOCUMENTS

| | | | |
|---|---|---|---|
| 4,881,553 A | 11/1989 | Grossman | |
| 5,109,871 A | 5/1992 | Thornton | |
| 5,314,917 A * | 5/1994 | Michaels | A61K 31/14 514/556 |
| 5,398,699 A * | 3/1995 | Fergus | A61F 6/04 128/844 |
| 5,458,114 A * | 10/1995 | Herr | A61F 6/04 128/842 |
| 5,477,865 A | 12/1995 | Broad, Jr. | |
| 5,513,652 A | 5/1996 | Schwartz | |
| 5,622,186 A | 4/1997 | Schwartz | |
| 5,626,149 A | 5/1997 | Schwartz | |
| 5,873,364 A | 2/1999 | Kopelowicz | |
| 5,885,205 A | 3/1999 | Kassman | |
| 6,298,852 B1 | 10/2001 | Manning | |
| 6,308,708 B2 | 10/2001 | Strauss et al. | |
| 6,321,751 B1 | 11/2001 | Strauss et al. | |
| 6,389,602 B1 | 5/2002 | Alsaffar | |
| 6,536,438 B1 | 3/2003 | Smith et al. | |
| 6,569,083 B1 | 5/2003 | Kassman | |
| 6,651,667 B2 | 11/2003 | Osterberg | |
| 7,434,581 B1 | 10/2008 | Reddy et al. | |
| 8,491,461 B1 | 7/2013 | Veslocki | |
| 8,651,110 B2 | 2/2014 | Hui | |
| 8,869,799 B2 | 10/2014 | Levy | |
| 9,351,866 B1 | 5/2016 | Resnic | |
| 2002/0189619 A1* | 12/2002 | Osterberg | A61F 6/04 128/844 |
| 2004/0099274 A1* | 5/2004 | Osterberg | A61F 6/04 128/844 |
| 2004/0194786 A1 | 10/2004 | Manning | |
| 2009/0090369 A1* | 4/2009 | Attila | A61F 6/04 128/844 |
| 2011/0073117 A1 | 3/2011 | Hui | |
| 2013/0014764 A1 | 1/2013 | Rojas | |
| 2013/0104904 A1 | 5/2013 | Hui | |
| 2013/0174852 A1 | 7/2013 | Resnic | |
| 2013/0316107 A1 | 11/2013 | Olseon et al. | |
| 2014/0076329 A1 | 3/2014 | Rhodes | |
| 2015/0047645 A1 | 2/2015 | Jumisco | |
| 2016/0038334 A1 | 2/2016 | Sedic | |
| 2016/0220412 A1 | 8/2016 | Vacco | |
| 2016/0250064 A1 | 9/2016 | Ross | |

FOREIGN PATENT DOCUMENTS

| | | |
|---|---|---|
| CA | 2170109 | 9/1996 |
| CA | 2171783 | 9/1996 |
| CA | 2700856 | 10/2011 |
| CN | 1174019 | 2/1998 |
| CN | 201157440 | 12/2008 |
| CN | 201157441 | 12/2008 |
| CN | 201208328 | 3/2009 |
| CN | 201248795 | 6/2009 |
| CN | 202060947 | 12/2011 |
| CN | 202173498 | 3/2012 |
| CN | 202184840 | 4/2012 |
| CN | 102488584 | 6/2012 |
| CN | 202654287 | 1/2013 |
| CN | 103096847 | 5/2013 |
| DE | 202013009517 | 1/2014 |
| EP | 0728453 | 2/1996 |
| EP | 0809989 | 8/1996 |
| EP | 1027381 | 8/2000 |
| EP | 1902692 | 3/2008 |
| GB | 1400332 | 7/1975 |
| GB | 2524398 | 9/2015 |
| IL | 108250 | 4/1997 |
| JP | H08/299375 | 11/1996 |
| JP | 2006289020 A * | 10/2006 |
| KR | 20030040750 | 5/2003 |
| RU | 2337650 | 11/2008 |
| WO | WO 1997/032549 | 9/1997 |
| WO | WO 1997/034551 | 9/1997 |
| WO | WO 02/100294 | 12/2002 |
| WO | WO 2011/159399 | 12/2011 |
| WO | WO 2014/041534 | 3/2014 |
| WO | WO 2014/058930 | 4/2014 |
| WO | WO 2014/116752 | 7/2014 |
| WO | WO 2015/168722 | 11/2015 |
| WO | WO 2015/174712 | 11/2015 |
| WO | WO 2016/043532 | 3/2016 |
| WO | WO 2016/055673 | 4/2016 |

* cited by examiner

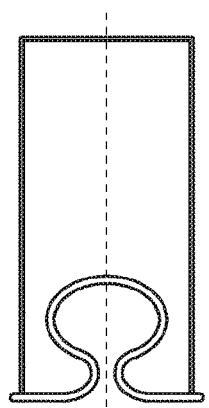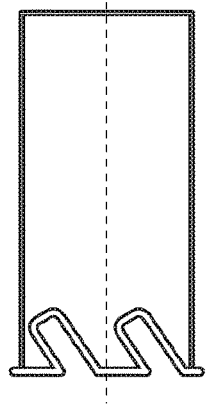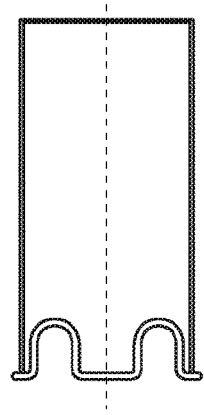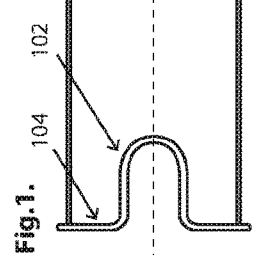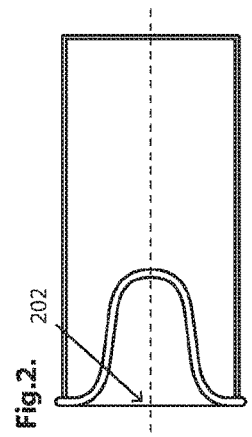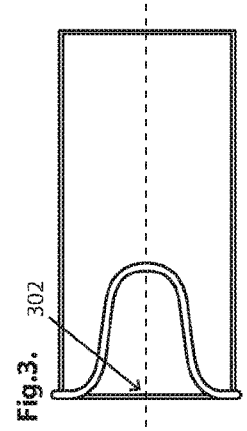
Fig.1. Fig.2. Fig.3.

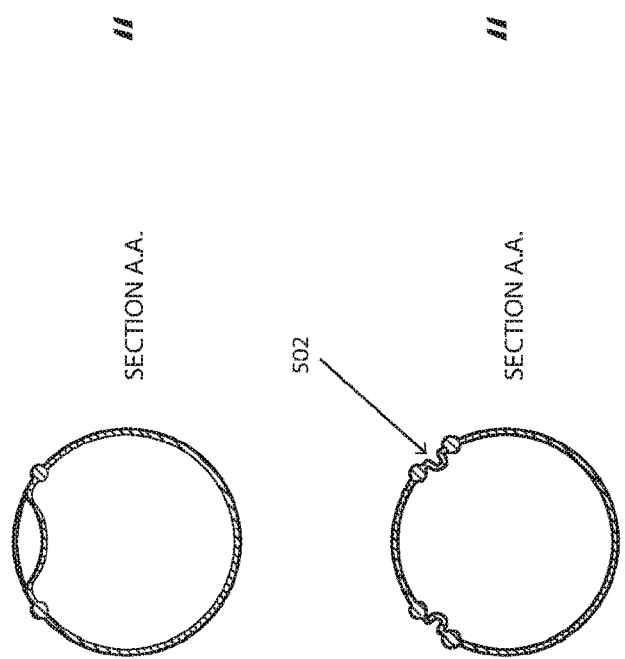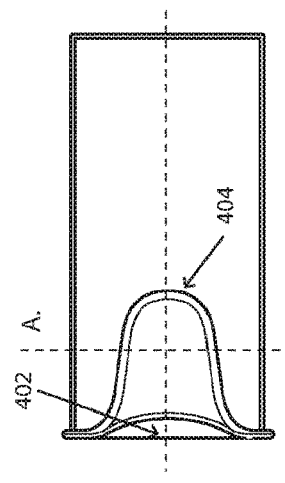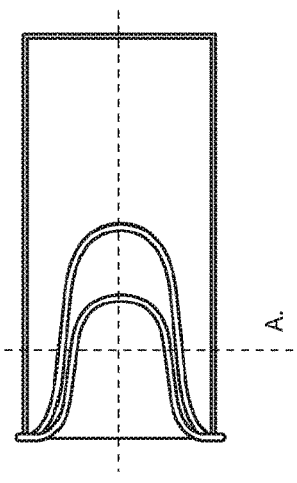

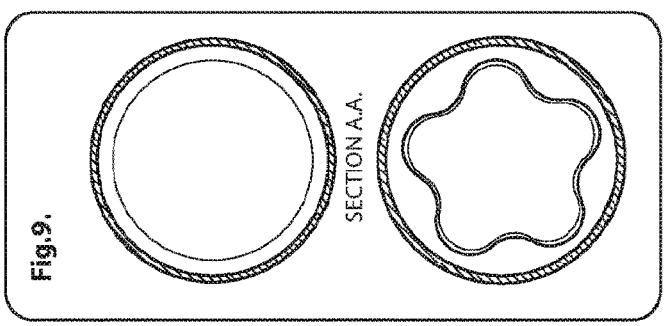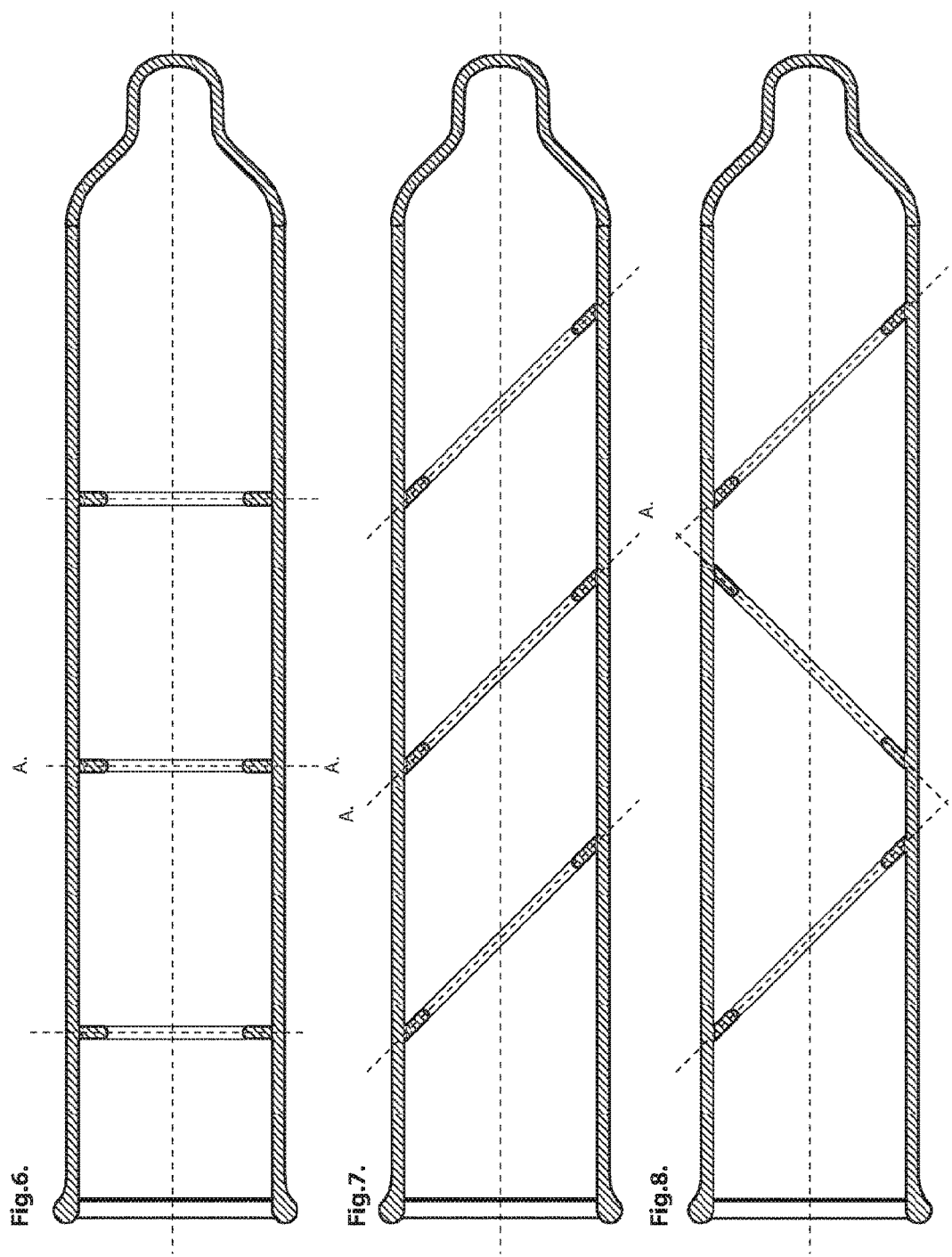

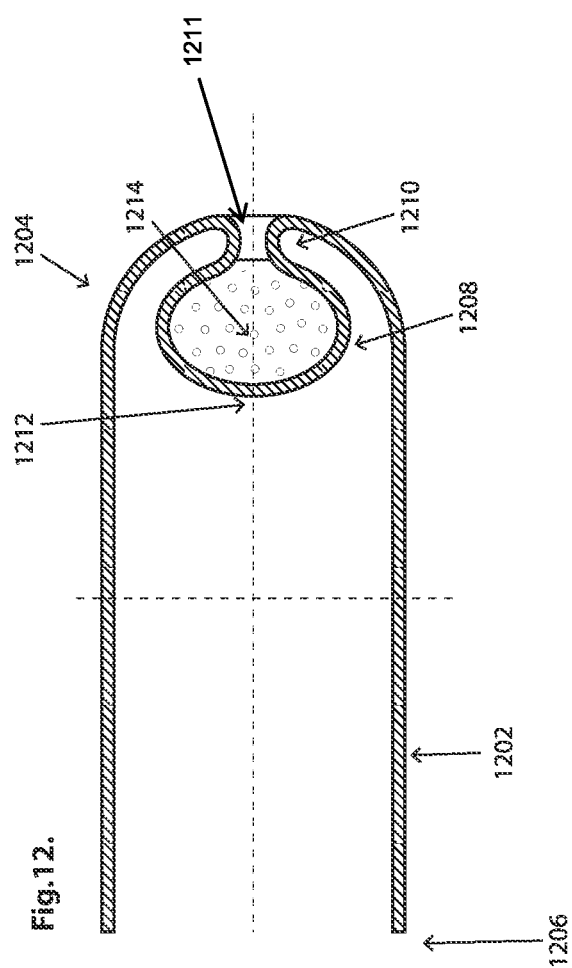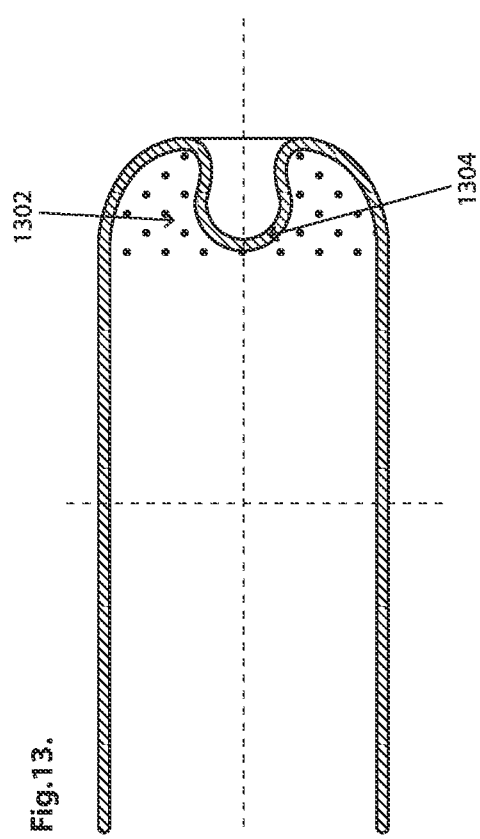

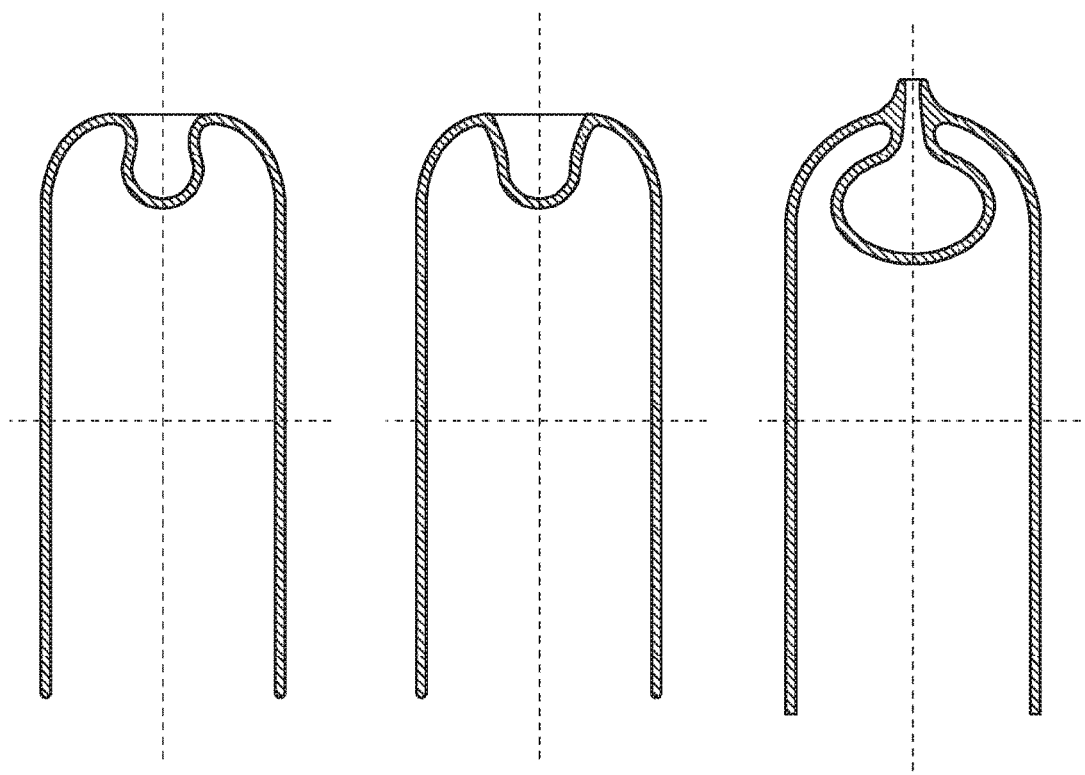
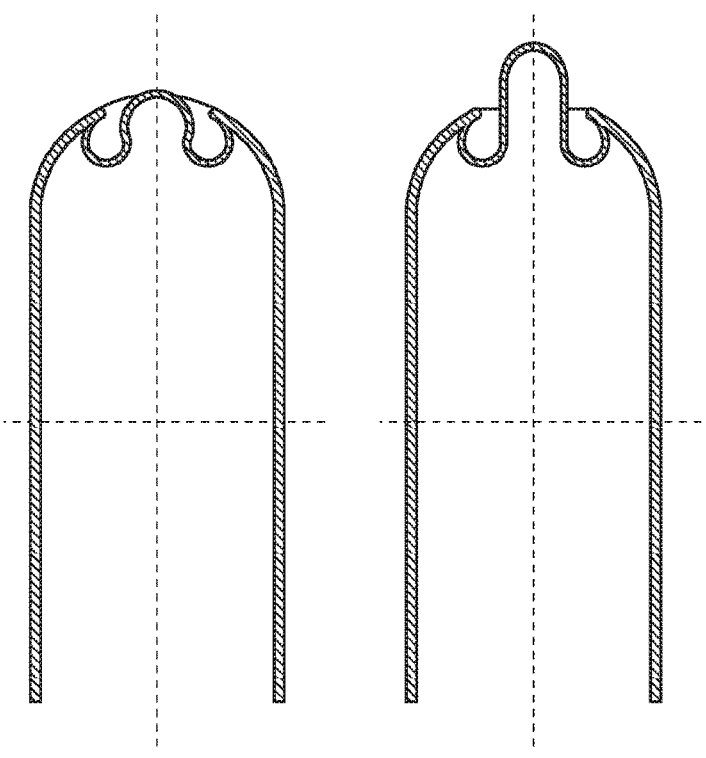
Fig.14.

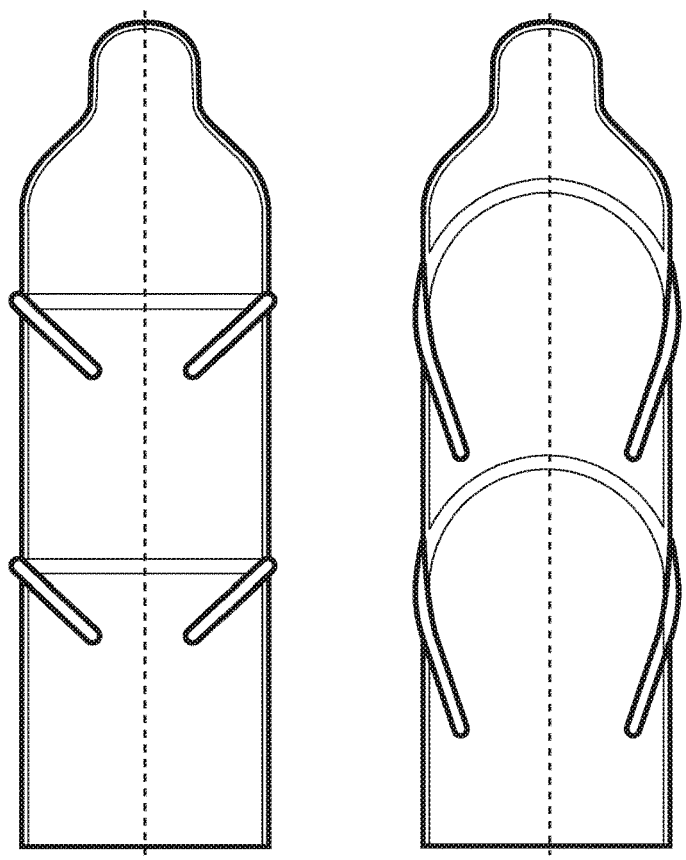
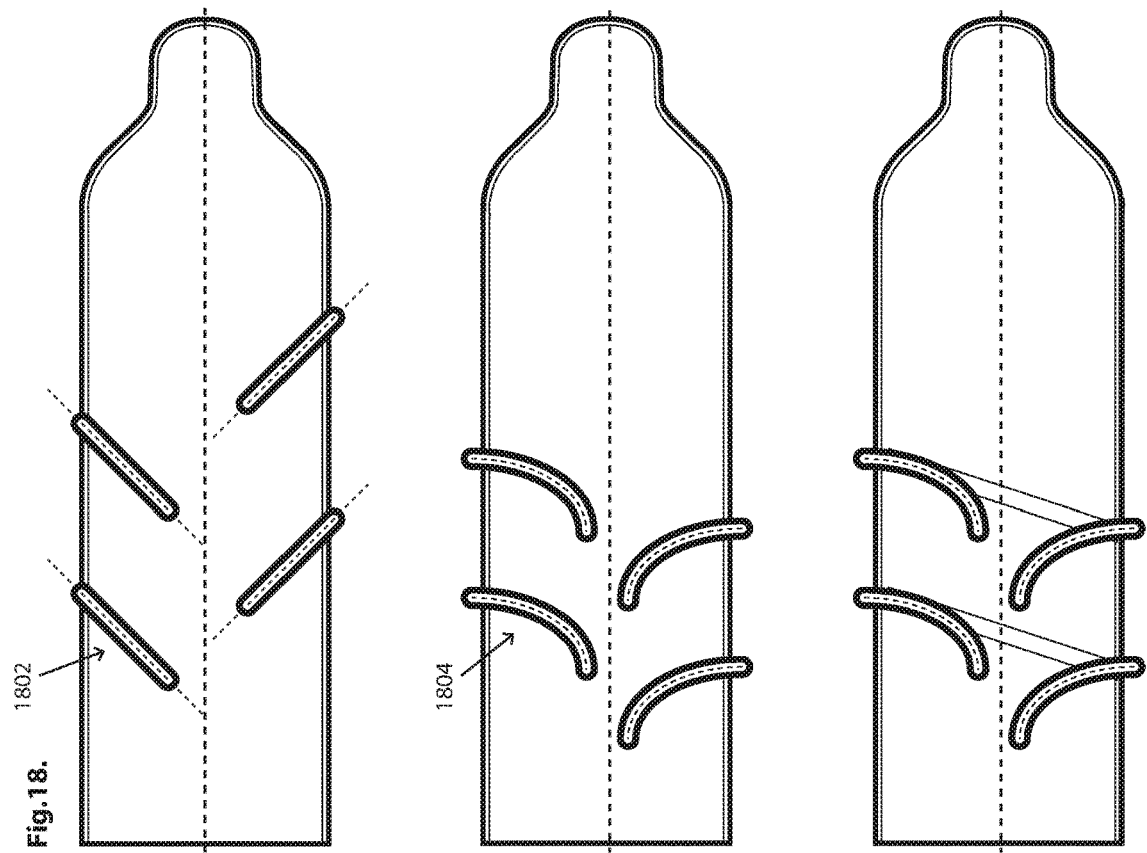
Fig.18.

CONDOMS

FIELD OF THE INVENTION

The present invention relates generally to prophylactic devices used both for birth control and prevention of sexually transmitted disease, and more particularly to a condom with one or more features to enhance stimulation of male and female partners, improve fit and comfort, reduce incidence of slippage and/or breakage, and support delivery and management of complimentary fluids such as lubricants and spermicides.

BACKGROUND TO THE INVENTION

Condoms in the form of a sheath typically comprising a continuous elastic tubular wall with a closed distal end and an open proximal end, are worn over the penis to help prevent conception and pregnancy and/or transmission of sexually transmitted diseases such as syphilis, *chlamydia* infections, genital herpes and HIV, for example, during sexual intercourse. They can also be used as a hygiene barrier during use with novelty sexual lifestyle products or 'sex-toys'. Condoms are typically composed of thin elastomeric materials, such as natural rubber latex or synthetic polyisoprene, acting as a barrier membrane while for maintaining sensitivity, and sensation during intercourse. Risk slippage and/or breakage and/or tear in a condom during sexual intercourse presents a concern due to the nominal thickness, and nature of the condom design, materials and manufacturing process. Potential for slippage and/or breakage and transmission of disease and or STIs and/or bacteria can be significantly impacted by contributing factors such as incorrect fit, incorrect application and use, and poor lubrication. More broadly the decision to use, or not use a condom can be significantly impacted by a range of factors including multisensory appeal, product accessibility, usability, social and societal influences, education and information, gender bias, and cultural issues. In retail-led markets users typically have access to a wide range of options to suit personal technical and sensory preference. However in some distribution scenarios the range of options may be limited, for example in vending machines, and some developed and developing country healthcare distribution frameworks, and therefore it is recognized as advantageous if an improved universal condom product is available.

Generally, condoms are manufactured during a dipping process, whereby an appropriately dimensioned and feature-embossed/de-bossed mandrel or mould former is dipped into a latex rubber, or alternative suitable material, emulsion, for example, formulated with complimentary additives such as curing agents, antioxidants, accelerators, odour masking scent or flavours to assist with the development of required properties and specification.

Once coated with the emulsion, the mould former is withdrawn, sometimes re-dipped a number of further times, and typically dried and cured to achieve the desired physical properties. Other additional or integrated processes may take place to add features such as ribs and dots. The cured condom is then stripped from the mandrel and rolled into a toroidal configuration. Other complementary processes such as washing, powdering, lubricating and testing also take place prior to packing. The condom may be restrained and contained in a number of typically oval or toroidal shapes in final packaging.

In use, the condom is operated typically by squeezing a formed teat at the closed distal end, to remove air and provide a handling point from which to unroll it down the longitudinal axis of the penis, or novelty lifestyle device.

The mechanical properties of condoms typically have to balance a number of competing and complementary functional and multi-sensory attributes. In particular the ability to achieve manufacturing consistency, barrier integrity, shelf life, material type, material thickness, surface texture, smell, feel, sound, and level of lubrication, among others to meet some specific requirements of condom standard(s) and certain other manufacturing specifications.

Changes in each of these specification parameters may impact on increasing or lessening risk of sheath integrity, and potential damage, slippage and/or breakage.

Changes in these parameters also impact on perceived fit and sensation—for example increasing of material wall thickness is widely believed to be correlated directly to a perception of reduced sensation, and in some design embodiments a less accommodating fit. Changes to design embodiment may also contribute to correct or incorrect use, such as incorrect orientation and operation of the rolled condom.

It is known in the art to include texture in the form of ribs or other projections along internal or external surfaces of a condom for the purpose of enhancing tactile sensation and stimulation of the male and female during sexual intercourse. Typically, the ribs or projections are integrally formed on a surface of the condom during the dipping process by embossed or debossed features resulting from respective grooves, notches or protrusions created in the surface of the mould former.

It is also known in the art to have a circumferential bead that is thicker in cross section than the general thickness of the sheath at the proximal opening, an intended consequence of the mould former stripping process during manufacture, which creates a locally thicker circular bead that helps with rolling the sheath prior to packaging, and provides a tighter barrier to potential of leakage of ejaculate and reduces risk of slippage during use.

A problem to be overcome in designing and manufacturing ribbed/textured condoms, and condoms with a thicker bead or rim at the open proximal end, is to avoid discomfort caused by localised circumferential bead tension, particularly apparent in an incorrectly fitting condom, while reducing potential for slippage and breakage during use, and unwanted conception and transmission of STIs'.

It is a challenge in free healthcare distribution channels (operating in both developed markets through sexual health clinics, doctors surgeries, and in developing markets, through NGOs, health charities and other healthcare, education and outreach organisations), and to a lesser extent in the retail market, that available products generally follow the median or 'universal' model for nominal technical attributes (such as fit, and preferential attributes such as surface feature, and lubrication type) which means that through drives for commercial, supply chain, retail, and distribution efficiency, choice of solutions to meet preference and anatomical distribution is typically limited. This may lead to unintended practical consequences such as discomfort and poor fit, which may result in behavioural consequences such as incorrect use, or future rejection, with resulting potential for increased incidence of unwanted conception and transmission of STIs.

Background prior art can be found in US2016/0038334 A1; WO2014/041534 A1; US2016/0250064 A; WO2015/168722 A1; CN103096847 A; US2016/0220412 A1; U.S. Pat. No. 9,351,866 B1; WO2016/055673 A1; WO2016/043532 A1; WO2015/174712 A1; GB2524398 A; US2015/

0047645 A1; WO2014/116752 A1; 202014/058930 A1; DE20 2013 009 517 U1; US2014/0076329 A1; WO2011/159399; US2013/0174852 A1; U.S. Pat. No. 8,651,110 B2; US2013/0104904 A1; US2013/0014764 A1; CA2700856 A1; US2016/0220412 A1; CN102488584 A; CN202173498 U; CN202060947 U; CN201248795 Y; CN201208328 Y; CN201157441 Y; US2004/0099274 A1; US2002/0189619 A1; U.S. Pat. No. 4,798,600; CN201157440 Y; U.S. Pat. Nos. 2,586,674; 4,881,553; IL108,250; EP0,728,453; EP0,809,989; U.S. Pat. No. 5,873,364; CN1,174,019; U.S. Pat. Nos. 5,885,205; 6,569,083; US2004/194,786; U.S. Pat. No. 6,298,852; KR2003/0,040,750; U.S. Pat. No. 8,491,461; CN202173498; CN202184840; U.S. Pat. Nos. 5,513,652; 5,622,186; WO97/32549; AU5,719,796; U.S. Pat. No. 5,626,149; WO97/34551; AU5,700,096; GB1,400,332; U.S. Pat. Nos. 5,109,871; 6,321,751; 6,308,708; RU2,337,650; CN202654287; JPH08/299,375; CA2,170,109; CA2,171,783; U.S. Pat. Nos. 7,434,581; 5,513,652; 6,389,602; EP1,027,381; US2013/316,107; U.S. Pat. No. 8,869,799 B1, U.S. Pat. Nos. 6,536,438, 5,477,865, WO2002/100294 A2; U.S. Pat. No. 6,651,667.

It would therefore be a significant advance in the art of prophylactic devices to develop a condom which provides enhanced sensation to both the male and female partner while providing improved universality of fit, improved comfort, and responds to a number of the use conditions that can increase the risk of incorrect use, and barrier integrity breach, including through slippage and breakage.

SUMMARY OF INVENTION

According to one aspect of the present invention there is provided a condom comprising: a continuous elastic tubular wall with a closed distal end and an open proximal end; and a teat at the closed distal end, wherein in use, the teat is retained partially or fully inside of the continuous elastic tubular wall, and the teat forms a chamber that is fillable with a fluid or phase change formulation which is released externally in use.

The teat may comprise a neck and a head, and the neck of said teat may be narrower than the head of said teat to retain the teat partially or fully inside of the continuous elastic tubular wall in use.

At least a portion of the continuous elastic tubular wall comprising the teat or around a base of said neck of the teat may be thicker than a remaining portion of the continuous elastic tubular wall to structurally retain the teat partially or fully inside of the continuous elastic tubular wall in use.

The teat may be prefilled with said fluid or phase change formulation during manufacture. Alternatively the teat can be filled by a user (for example by using a suitable device). The fluid may be a lubricant, anti-viral, stimulant, anaesthetic, or spermicide.

The condom may further comprise a frangible seal arranged to release said fluid or phase change formulation in response to movement and/or pressure immediately prior to or during use. Alternatively, the condom may further comprise a user operable seal arranged to release said fluid or phase change formulation in response to manual input prior to or during use.

The condom may be configured to capture seminal fluid in a toroidal void around the teat during use.

According to another aspect of the present invention there is provided a condom comprising: a continuous elastic tubular wall with a closed distal end and an open proximal end; a teat at the closed distal end; and wherein the continuous elastic tubular wall has at least one raised feature, each of the at least one raised feature having a portion arranged at an angle relative to a longitudinal axis of the continuous elastic tubular wall, and in use create a local force on the continuous elastic tubular wall at an angle to the longitudinal axis in response to engagement with a receiving body.

The at least one raised feature may be straight or curved.

The continuous elastic tubular wall has an interior surface and an exterior surface, and the at least one raised feature may be formed on the interior surface, the exterior surface or both the interior surface and the exterior surface.

The portion may be arranged at an acute angle relative to a longitudinal axis of the continuous elastic tubular wall.

The at least one raised feature may be symmetric about the longitudinal axis.

The at least one raised feature may be symmetric about a plane transverse to the longitudinal axis.

In use, in response to movement along the longitudinal axis, the at least one raised feature may contract the tubular wall between the at least one raised feature and may expand the tubular wall outside the at least one raised feature.

The at least one raised feature may be non-symmetric about a plane transverse to the longitudinal axis.

In use, in response to movement in a first direction along the longitudinal axis, the at least one raised feature contract the tubular wall between the at least one raised feature and expand the tubular wall outside the at least one raised feature; and in response to movement in a second direction along the longitudinal axis, the at least one raised feature expand the tubular wall between the at least one raised feature and contract the tubular wall outside the at least one raised feature.

The different aspects of the invention described above may be combined.

In one, or a combination of the aspects of the invention described above, the condom may have further features:

The condom may further comprise a retaining feature towards its base which extends circumferentially around the condom and which incorporates a stress relief feature comprising one or more loops which extend along the tubular wall for a length. The retaining feature and the one or more loops may be thicker than the tubular wall. The stress relief feature may comprise a web enclosed by each of the one or more loops. The web may have approximately the same thickness as the tubular wall. The web may comprise a bead towards the base of the condom. The bead may have the same thickness as the retaining feature. Alternatively the bead may be thinner than the retaining feature. The bead may be thicker than the tubular wall. In some embodiments an area enclosed by each of the one or more loops is void.

Alternatively or additionally, the condom may further comprise a seminal fluid retention feature comprising one or more internal inward protruding protrusions extending partially or completely circumferentially around the condom arranged to retain seminal fluid in the condom. The one or more internal inward protruding protrusions may be arranged approximately perpendicular to the continuous elastic tubular wall. The one or more internal inward protruding protrusions may be arranged at a non-perpendicular angle to the continuous elastic tubular wall. A portion of each of the one or more internal inward protruding protrusions may be arranged in parallel with the continuous elastic tubular wall. One of the one or more internal inward protruding protrusions may be provided at the base of the condom. The condom may further comprise a retaining feature at the base of the condom.

Alternatively or additionally, the condom may further comprise a longitudinally extended portion of thickened material at its base formed by a portion of the continuous elastic tubular wall being folded over at the open proximal end and adhered to, and/or integrated into, the tubular wall for a part of the length of the condom. The portion of the continuous elastic tubular wall folded over at the open proximal end and a remaining portion of the continuous elastic tubular wall may be made of a first material. The portion of the continuous elastic tubular wall folded over at the open proximal end may be made of a first material and a remaining portion of the continuous elastic tubular wall may be made of a second material, wherein the first material is different to the second material. The first material may be less or more elastic than the second material. The first material may have a mesh structure.

BRIEF DESCRIPTION OF THE DRAWINGS

For a better understanding of the present invention and to show how embodiments may be put into effect, reference is made to the accompanying drawings in which:

FIGS. 1-5 illustrate various configurations of a condom having a base bead loop feature;

FIGS. 6-11 illustrate various configurations of a condom having a baffle feature;

FIGS. 12-14 illustrate various configurations of a condom having a complementary fluid delivery teat feature;

FIGS. 15-19 illustrate various configurations of a condom having a one or more contraction feature;

DESCRIPTION OF THE INVENTION AND SOME PREFERRED EMBODIMENTS

Figure 10:
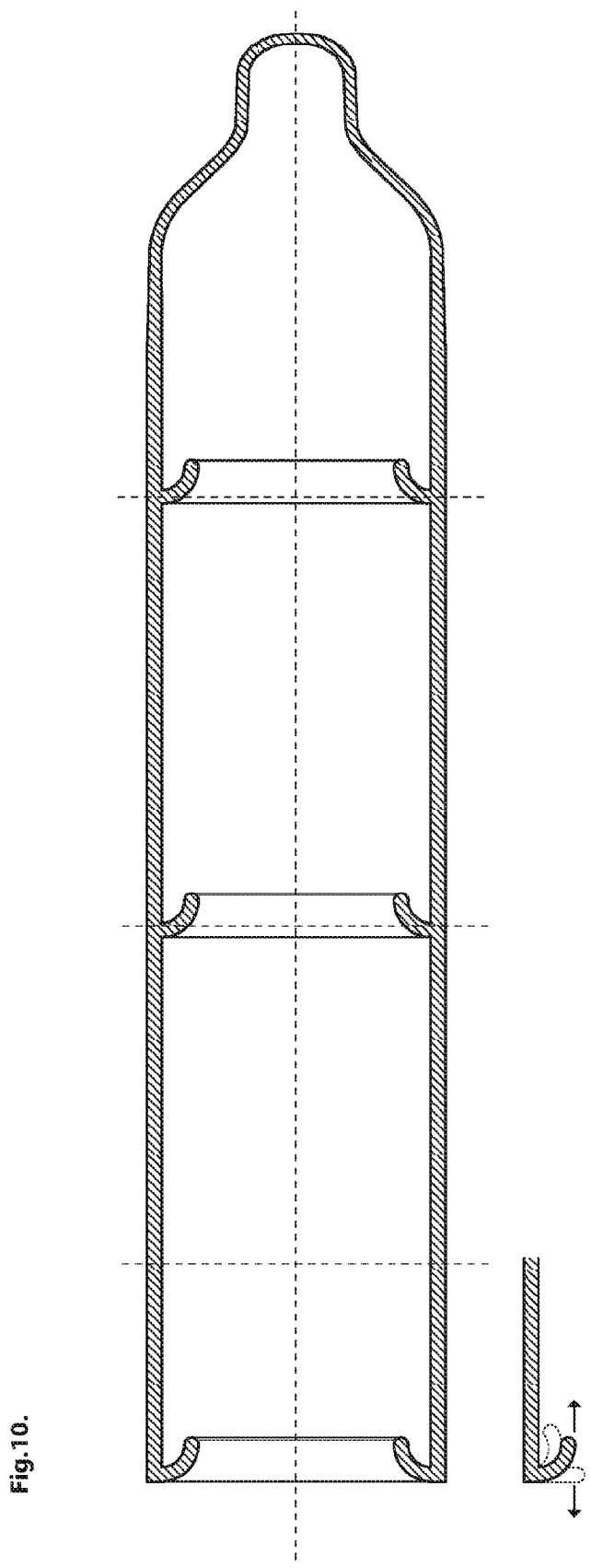

According to the present invention there is therefore generally provided a condom comprising a continuous elastic tubular wall with a closed distal end and an open proximal end and further improving features.

Base Bead Loop

In particular, one aspect of the present invention is directed to a condom which comprises: a continuous elastic tubular wall including a closed distal end and an open proximal end; and at the open end, the thicker proximal hooped bead in a preferred embodiment has one or more elongated, thicker, locally looped projections. These may extend in to or upon the tubular wall for a length. The looped return profile design may be tailored to a particular target specification, aesthetic, fit profile or sensory outcome. This has the purpose of providing greater elastic flexibility of the proximal bead or rim feature, by providing a lengthened overall circumference while maintaining structural characteristics that reduce the potential for tearing of the main tubular wall beyond the feature.

Thus in some aspects the condom has a (preferably elastic) retaining feature towards its base which extends circumferentially around the condom and which incorporates a stress relief feature comprising one or more loops or meanders able to be partially or wholly straightened to allow the circumference of the condom to increase. The retaining feature may comprise a part of the condom moulding, or an overmoulding, and/or a separate linear metal, plastic or elastic part incorporated into the condom.

In one embodiment this stress relief bead feature or loop has no web between the projection loop feature (otherwise referred to herein as a retaining feature) (102) (FIG. 1) but the thickness of the bead (104) and projected loop provide sufficient structure to maintain adequate determined rigidity and nominal tube diameter.

In another embodiment there may be a partly constraining web (202), for example of approximately the thickness of the main elastic tubular wall between the localised, elongated loop projections (FIG. 2).

In a further embodiment there is a partly constraining web (302) of e.g. approximately the thickness of the main elastic tubular wall between the localised, elongated loop projections. This may additionally have a localized, continued, proximal (to the base) bead between the elongated features for example of an alternative thickness, for example, which is dimensionally similar or less than the main bead and preferably greater than the thickness of the main tubular wall (FIG. 3).

In a further embodiment, multiple loops (402, 404) extend from the along the open proximal end, along the axis of the tubular wall (FIG. 4) and/or and in some variations may have a small concertina segment (502) when viewed in cross section (FIG. 5) by virtue of intended localised variance in wall tension enabled by creation of these features.

Further variations can be envisaged by using the described features in various combinations, and/or with other integrated and/or surface features such as ribs, dots, hatching, biaxial mesh or other patterns and textures. It is also an advantage of embodiments of this invention that the relationship of the bead loop to the open proximal end and tubular wall, including shape, length and angle are such as to continue to function partly or completely as intended, without causing discomfort in the instance that the condom is not fully unrolled.

The invention also provides a manufacturing process to create this feature. In embodiments this uses a multi-stage dipping process during which the condom mould former is dipped one or more times, and the elongated bead feature is created through a localised partial stripping and relocation of material which creates the one or more localised loops. The partial stripping may for example take place at the end of the dipping cycle, to allow partial curing of the bead feature before full stripping, or between the dipping cycles to fix the elongated one or more axial looped bead features within the wall of the sheath or web, as shown in the drawings.

An alternative manufacturing process provides for the local bead loop projections to be integrally formed on a surface of the condom during the one or more stages of the dipping process by features created in the surface of the mould former.

A further alternative manufacturing process provides for a separate pre-formed elongated loop manufactured of a material providing the appropriate properties and assembled as a co-mould, laminate or composite to the former prior to or during the dipping process to ensure robust material synthesis.

Thus the stress relief feature may be either a composite of a pre-manufactured and assembled loop, or provided by the manufacturing process, for example using a localized brush down and retention of an appropriate loop shape after the first dip, and optional further dips to fix it in place within the tubular wall.

The term "loop" can also be described as a "bead".

In embodiments, the base ring bead (or loop) is combined with other features described herein.

In an embodiment, the condom combines the base bead with the complementary fluid teat. Advantageously, the circumference of a condom is able to vary more than condoms without the described base bead. Therefore, an embodiment provides a condom which can fit a more diverse range of users than a traditional condom as disclosed in the prior art, and provide a more comfortable experience. Furthermore, the retaining feature of embodiments complement the extra lubrication of the complementary fluid teat. Although lubrication can reduce tearing during use, lubrication can also in some circumstances increase slippage of the condom during use. Therefore, the two features can be combined in a synergistic and complementary fashion.

Embodiments of the present invention can also provide additional benefits. A restrictive base bead element can help overcome problems of Erectile Dysfunction. However, a rigid restrictive base element as disclosed in prior art can cut off too much blood supply to the penis and cause health problems if the element is worn for too long a period. Embodiments of the present invention provide a more distributed restrictive pressure to the circumference of the penis and hence can assist intercourse in the instance of Erectile Dysfunction. In an embodiment, the condom can also have an elastic flexibility provided by features such as the hoop, bead, web (or other features described herein). This means that the restrictive pressure on the base of the penis is less likely to cause health problems because of the elastic properties of the described features of the present invention.

In embodiments, a condom provides for increased circumference of the base bead without sacrificing the uninterrupted integrity and contact pressure of the bead around the open end therein. Thus supporting increased comfort at the base of the penis without increasing the chance of breakage and/or slippage, and/or fluid leakage. A further advantage is that the loop extending into the condom wall and towards the closed distal tip increases localised stiffness of this part of the wall, thus providing increased integrity, and further providing sensory advantages for both partners.

Baffle

In another aspect of the present invention, the condom comprises: a continuous elastic tubular wall including a closed distal end and an open proximal end; and on the interior of the tubular wall one or more internal protrusions extending partially or completely circumferentially, and configured as an inward protruding, for example circumferential wall to form a thin internal 'baffle' of locally reduced cross-section which may be approximately perpendicular to the continuous elastic tubular wall (FIG. 6). The baffle is flexible by virtue of the moulded material properties and when worn on the penis provides for a number of benefits including increased seminal fluid retention in chambers nearer the closed distal end, increased sensation, and improved inclusive universality of fit, as the overall diameter of the continuous elastic wall of mass market variants may be increased due to the role of the baffles in reducing slippage and potential for body fluid leakage, and assisting sheath retention of the now increased continuous tubular wall diameter. A further benefit of this configuration is the increased compressive strength, and reduced bead stress in embodiments through a localised increase of the wall thickness at each baffle feature, as when fitted the penis folds the baffle broadly parallel to the tubular wall.

In a related approach, the one or more circumferential internal protrusions may be configured as an inward protruding toroidal wall to form a thin internal 'baffle' of locally reduced cross-section is arranged at a non-perpendicular angle to the continuous elastic tubular wall (FIG. 7), providing for an extended circumference, for the given nominal main tube axial diameter, while providing the benefits of reducing slip and potential for leakage. An alternative non-perpendicular arrangement is shown in FIG. 8.

In a further embodiment the one or more circumferential internal protrusions may be configured as an inward protruding for example circumferential wall to form a thin internal 'baffle' of locally reduced cross-section. This may have various alternative shapes including circular, and petaloid or non-circular lip on the inward edge of the baffle to increase elasticity, lip circumference and minimise discomfort and development of pressure points that may increase risk of tearing (FIG. 9).

Figure 11:
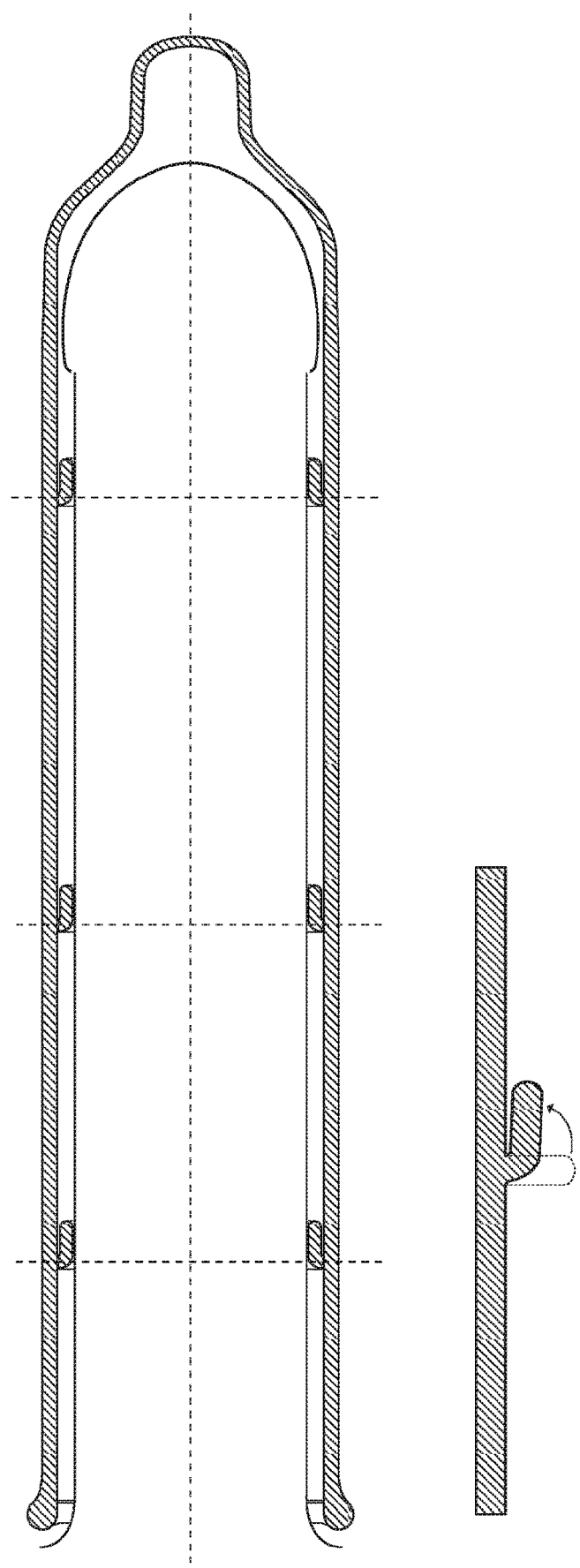

In a further embodiment, the one or more circumferential internal protrusions configured as an inward protruding wall to form a thin internal 'baffle' of locally reduced cross-section may be arranged at the open proximal end of the continuous tube with the baffle formed as well as or in place of the traditional thicker proximal rim bead (FIG. 10), thereby reducing the localised constriction typically experienced by the traditional bead when applied, due to the baffle folding internally (FIG. 11) and in embodiments creating a improved thicker wall arrangement which distributes tension across a larger surface area, providing increased comfort and security against leakage after ejaculation.

In embodiments the internal protrusions of the type described above and/or shown in FIGS. 6-11, extend inwardly from an inner wall of the condom and engage the outer surface of the penis in use.

In embodiments, a condom has one or more flexible features protruding into the condom interior to engage with the penis, to reduce breakage and/or slippage, and leakage of seminal fluid. Advantageously, nominal condom diameter may be increased as long as the baffle features maintain contact. This benefits user comfort and provides for a greater universality of fit, without sacrificing integrity and risk of slippage and/or breakage.

Complementary Fluid Delivery Teat

In another aspect of the present invention, the condom comprises: a continuous elastic tubular wall (1202) including a closed distal end (1204) and an open proximal end (1206); and at the closed distal end (1204), a shaped teat (1208). The neck (1210) of the teat may be formed in such a way as to be narrower than the head (1212) of the teat.

In some embodiments the teat is formed such that when turning the condom inside out, the head (1212) of the teat is located fully or partially on the inside of the elastic tubular cylinder, creating a void which can be filled by the manufacturer or user with lubricant, spermicide, alternative complementary fluidic or phase change material (1214) (FIG. 12). In other embodiments the teat may be formed on the outside of the condom and later locally turned in, rather than the whole condom being turned inside out. This may be achieved using a former which has a narrow teat neck; the teat may then be located inside as a later operation. Localised structure and form create bi-stable operation and location of the teat.

In embodiments the combination of tension, form, and engineered mechanical properties in the condom material, revised teat structure and fluid filled teat chamber negate the need to pinch the tip to evacuate the air in some variations, thus improving the condom application process. The seminal fluid (1302) is captured in the toroidal void around the internal teat (1304) (FIG. 13). The aperture cross sectional area or gap between the teat, teat neck and adjoining rim, and neck length may be adjusted for a desired release rate of the complimentary fluid, and ease of user handling and condom application. That is, the specification for the cross section of the neck of the teat, and/or teat opening may specifically provide for a relationship defined by and with the fluid rheology to achieve preferential delivery such as, but not limited to time or applied pressure, of the complementary fluid or phase change material.

In embodiments this chamber may be continuously open, relying on the rheology of the fluid to enable timely dispensing, or release via a frangible or user operable seal. It will be apparent that the teat chamber has no fluidic communication with the interior of the condom.

The complimentary fluid may thus can be delivered in a controlled and targeted way during initial penetration, and subsequent intercourse, managing unwanted complementary fluid spread and mess. Compression exerted against the fluid filled teat by the head of the penis is also intended to offer some sensory advantage.

In other variations of this design the teat shape/region may thus be modified to offer one or more features which complement the described structure and purpose, and additionally to assist with evacuation of air, location and application (FIG. 14).

The manufacturing process to create this feature is also an aspect of this invention. This uses a multi-stage dipping process during which the condom mould former is dipped multiple times, at least one of which is only a partial dip of the closed distal end providing increased thickness and structure locally for the teat. During stripping from the mould former, or a subsequent processing operation, the head of the teat is located on the inside of the elastic tubular cylinder, creating a void which can be filled with lubricant, spermicide, or alternative complementary fluidic.

In embodiments, the condom allows the possibility of lubricants, spermicides, or alternative complementary fluidics to be used in conjunction with the condom that may not be compatible with condoms of the prior art. Lubricants, spermicides, or alternative complementary fluidics with varying viscosity, rheology, phase change and other properties can be managed by selecting fluids with properties that are suitable for storing in the void. Advantageously, this can utilize lubricants which may not be compatible with condoms of the prior art.

In embodiments of the manufacturing process, the material at the neck of the teat may be locally thickened and/or reinforced to provide local structural mechanical properties which retain the teat inside of the continuous elastic tubular wall in use. This allows the head of the teat to be positioned on the inside of the elastic tubular cylinder after the condom has been turned inside out during manufacture. In embodiments the locally narrower neck allows for the teat to be turned inside out without additional thickening of material.

An embodiment of the condom provides containment and controlled delivery of complementary fluids, including but not restricted to lubricants, spermicides, stimulants, anaesthetics, flavours, and pharmaceutical solutions such as antivirals, to provide opportunity for increased comfort, safety, alternative sensory experience, and help reduce incidence of breakage. Opportunities are offered in particular by fluids with thixotropic properties, to assist localised application and retention in the teat at manufacture, and reduced spillage and improved targeted application in use. Fluids may be added at point of manufacture, or by the user with the assistance of further apparatus, packaging or dispensing solutions, according to personal preference, before use.

The teat may display bi-stable properties thus being able to emerge partially or fully from inside the continuous elastic tubular wall during use.

Contraction Features

Figure 15:
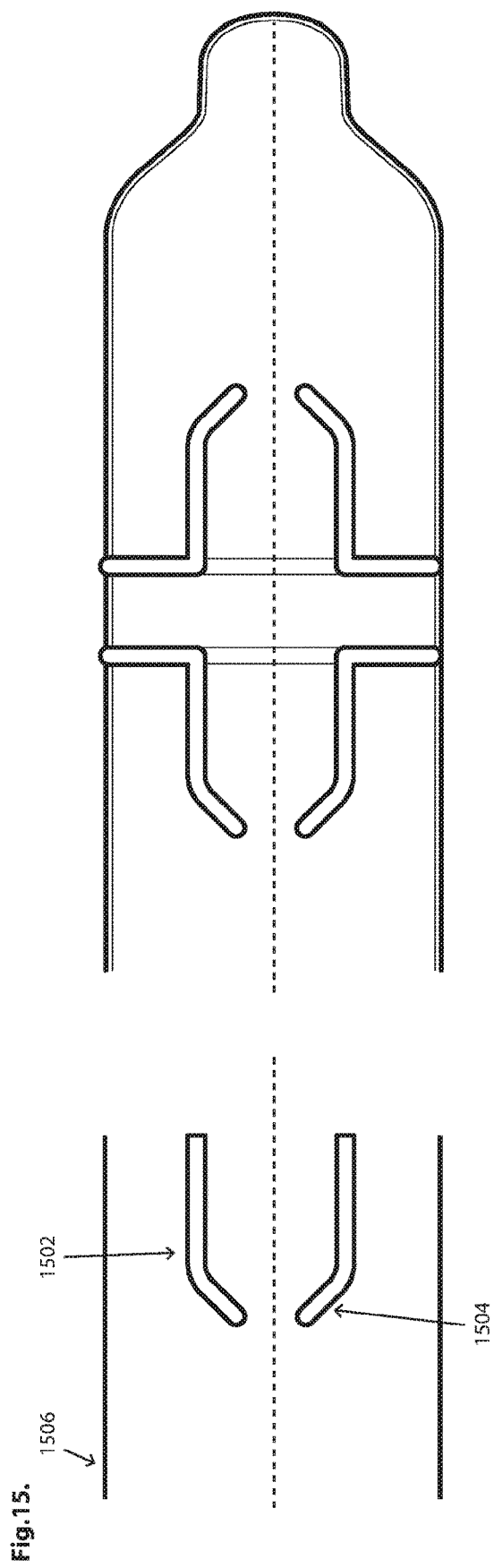

In another aspect of the present invention, the condom comprises features intended to reduce the incidence of the slippage element of the standardised industry protocols for Breakage and Slippage. Thus this aspect provides a condom with a continuous elastic tubular wall including a closed distal end (1606) and an open proximal end (1608); and at the closed distal end, a shaped teat (1610). The continuous elastic tubular wall has one or more straight or curved longitudinal raised (1502, 1602, 1902) projecting features (otherwise referred to herein as raised features 1502, 1602, 1702, 1802, 1902) which are, for example, dip moulded or applied via a printing or other additive process, and in which at least part of an individual feature is arranged an (acute) angle to the axis (1504) of the continuous elastic tube (1506) (penis longitudinal axis) and whose purpose is to create a lead-in that infers a local force (1604) on the tubular wall at an angle to the axis of relative movement when engaged with a receiving (broadly) tubular orifice (otherwise referred to herein as a receiving body) in response to friction (FIG. 15).

In embodiments, it can be seen that there is a functional relationship between one or more clusters of two broadly symmetrical angled features which work together to create a local force on the continuous elastic tubular wall at an angle to the longitudinal axis in response to engagement with a broadly tubular receiving body.

Figure 16:
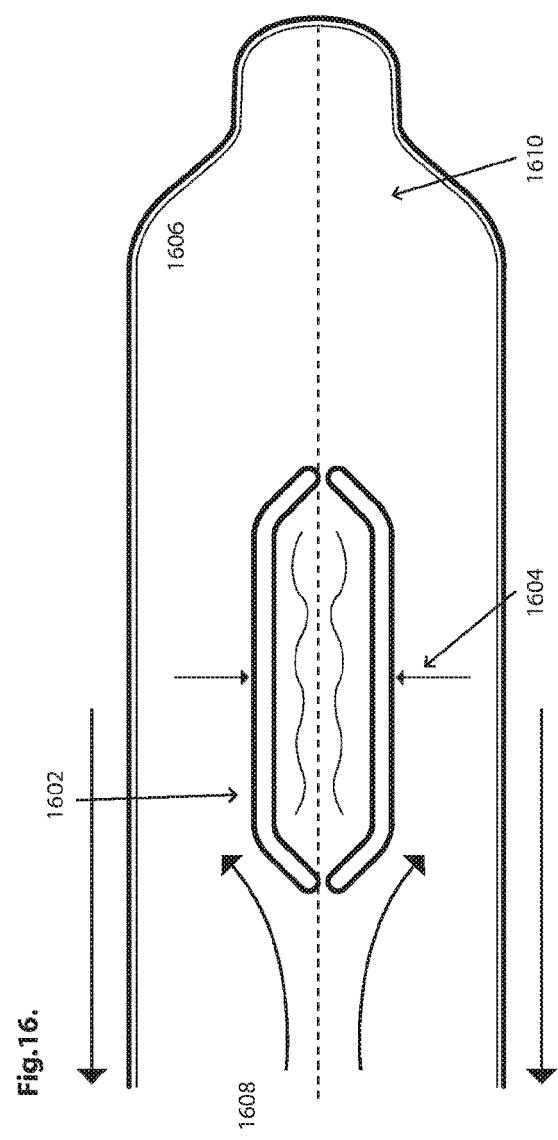

FIG. 18 shows different example patterns of angled features (1802, 1804) that are examples of features symmetric about a longitudinal axis. This class of feature when moved relative to the orifice in direction from right to left as drawn, create frictional forces that tend to dynamically encourage the features towards each other, thus providing a marginal local tightening of the tubular wall outside the pair of features and partial relaxing the wall in between the features. This can provide sensory and functional benefits. In embodiments, when moving in the opposite direction the opposite effect occurs. FIGS. 15, 16, 17 and 19 show example designs that are also symmetrical about a line parallel to the longitudinal axis lying in the surface of the tubular wall (i.e. about a radial plane). Additionally or alternatively any of the previously described designs may be symmetric about a plane transverse to said longitudinal axis. This arrangement creates the tightening effect and localized pulsing sensation outside the features in both directions of relative motion (FIG. 16).

Figure 19:
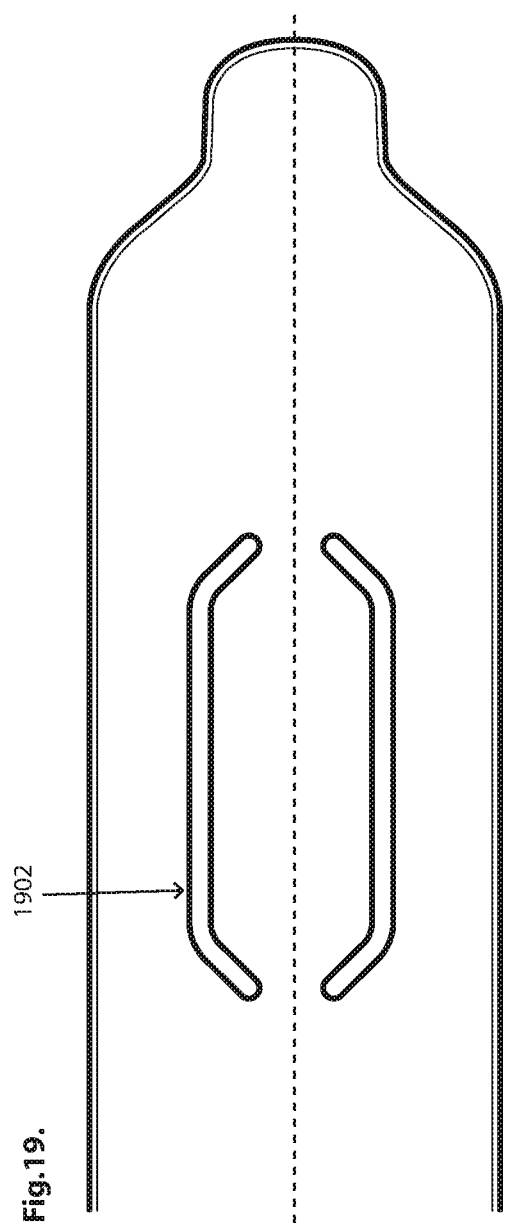

In contrast to FIG. 16, FIG. 19 shows when the worn condom is stationary between movements during use, for example, when the linear movement has paused and withdrawal is about to begin. At this time, there is no movement of the condom and so there are no frictional forces. This results in the features retracting and returning to their "neutral worn position" (noting the natural tension defined in the wall implied through wearing said prophylactic) i.e. their 'undynamic' state when not reacting to external forces.

Dipping or an additive manufacturing process may be optionally used for the application of such features.

The patterns can be present on the inside and/or the outside of the tubular wall.

Advantageously, embodiments can provide a condom with a larger nominal diameter that is still secure during use. Therefore, embodiments can provide condoms which are more universal than prior art. Due to the tightening of the tubular wall during use, a condom with a larger nominal diameter can be used securely. This means that embodiments provide a condom suitable for a more universal user group, a particular advantage in some distribution situations where a greater range of options is limited, including in vending machines, and some healthcare distribution frameworks in both developed and developing countries.

Advantageously, embodiments can provide a condom with angled contraction features in combination with a complementary fluid delivery teat. Whilst lubricant can be used to reduce breakage and may provide enhanced sensation, lubricant may also have the effect of increasing risk of slippage of the condom in some circumstances. When the angled contraction features are provided in an embodiment in combination with the complementary fluid delivery teat, the angled contraction features may provide additional dynamic constrictive force, thus aiding the objective of reducing slippage. Therefore, embodiments of the present invention may provide additional benefits of reduced slippage and reduced breakage.

Figure 17:
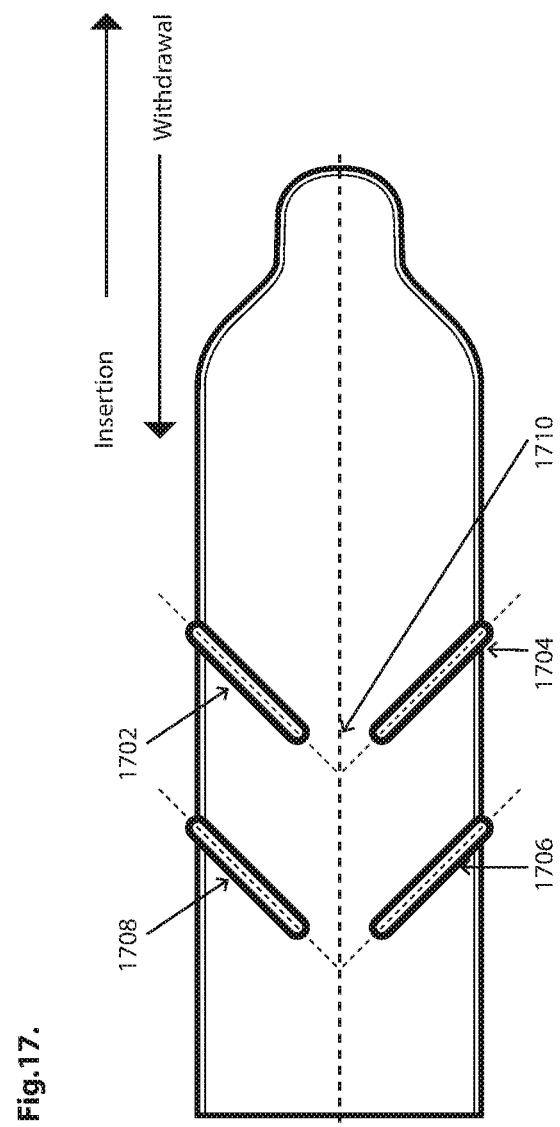

During withdrawal (first direction) of the condom from the tubular orifice, shown from right to left in FIG. 17, the part of the condom occupying the space between the features (1710) contracts (reducing the tension in the tubular wall). The part of the condom occupying the space outside the features elastically deforms (stretches). This causes a localized tightening effect, meaning slippage is less likely to occur.

During insertion (second direction) of the condom into the receiving body, shown from left to right in FIG. 17, frictional forces between the features (1702), (1704), and the receiving body cause the features (1702, 1704) to move apart from each other. Therefore, the part of the condom occupying the space between the features (1710) stretches creating a local area of higher material tension, whilst the part of the condom occupying the space outside of the features contracts.

FIG. 18 also shows alternative possible configurations of surface features which would achieve similar effects utilizing the same principle. FIG. 18 illustrates configurations in which a single surface feature may be provided; see for example the rightmost configurations and the bottommost configuration (multiple features are shown in these configurations but as an alternative only a single one of these features may be provided)

Advantageously, the effect of the surface features means that nominal condom diameter may be increased to benefit user comfort and universality of fit, without sacrificing or with minimal impact on integrity and risk of slippage and/or breakage.

In embodiments, a condom may have features like those proposed in FIGS. 15, 17, 18 formed instead or additionally on the inside wall of the condom. Advantageously, this would have the added benefit of engaging with features of the surface of the penis to further reduce potential for slippage.

It will be appreciated that local contraction of the tubular wall reduces the local tension in the tubular wall and local expansion of the tubular wall increases the local tension in the tubular wall.

Base Bead

Figure 20:
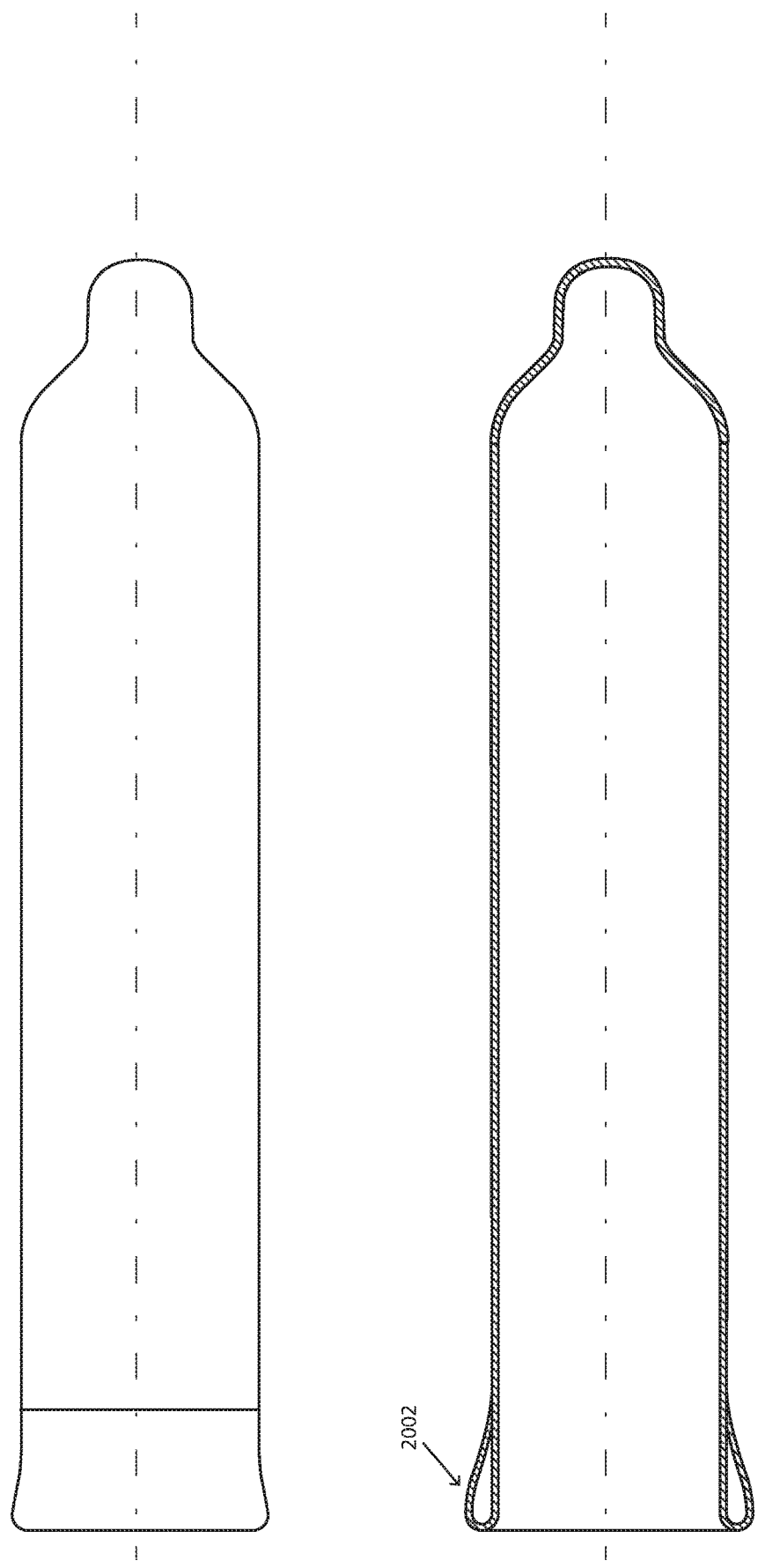
FIGS. 20 & 21 illustrate various configurations of a condom having a base bead feature.

In another aspect of the present invention, the condom comprises: a continuous elastic tubular wall including a closed distal end and an open proximal end; and at the open proximal end of the continuous tube, in place of or additional to the traditional thicker rim bead, a portion of the continuous tubular wall may be folded over from the bead and adhered and/or integrated into the continuous wall for part of the length of the condom extending from the open end towards the closed distal end, thereby creating a longitudinally extended portion of thickened, for example, double layer material (2102, 2002). The walls may be partially or fully adhered together or be able to slide against each other. Both designs provide a greater bead surface area of reinforced contact material compared to existing designs, and thus maintain safety while reducing the localised constriction typically experienced by the traditional thin proximal rim bead when worn (FIG. 20).

Figure 21:
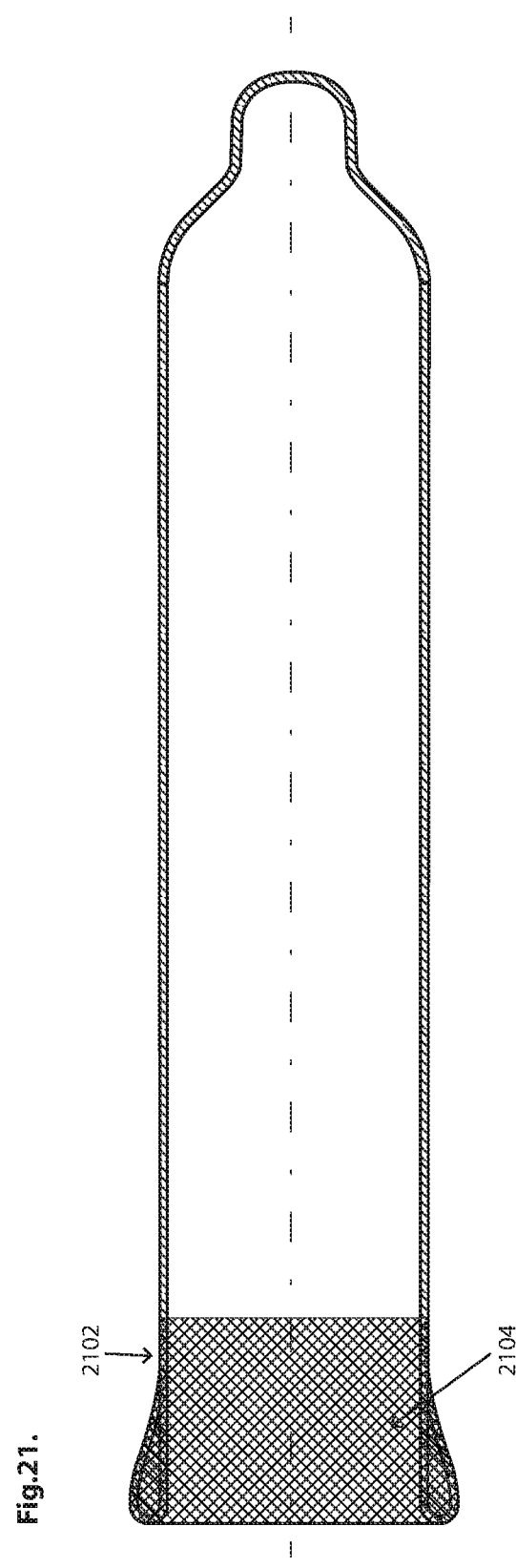

In a further example of this approach the continuous elastic tubular wall including a closed distal end and an open proximal end has at the open proximal end, in place of (or additional to) the traditional thicker bead loop, has an (interlocking) mesh (2104) or other structure on or within the tubular wall extending along at least a portion of the wall. The structure may be formed by the same manufacturing process as that used for the elastic wall, or by a composite with a second material, that may be less (or more) elastic, and folded over thereby forming a bead which is more comfortable and less restrictive than traditional configurations (FIG. 21).

In still other examples of this aspect an anisotropic base bead or region may be provided for the condom in other ways.

Thus the invention also provides a method of reducing localised compression at the bead around the open, base end of the condom, in particular by fabricating an integrated or composited mesh or lengthened roll-over area.

In embodiments of the condom/method, particularly but not essentially those using a mesh, the thickened base region of the tube does not substantially increase the compression/restriction around the base of the penis but instead aims to provide integrity of fit at this point by having increased thickness over a larger area, without the substantially increased overall compression. Thus in embodiments, as shown in FIG. 26, the mesh is preferably embedded (or otherwise incorporated into the condom) in a 'relaxed' state which does not allow significant further (biaxial) tightening that would deliver an increased restriction.

In embodiments, a condom provides localised thickening and/or compositing of base bead at the open proximal end, including but not limited to biaxial woven composite. Advantageously, this reduces breakage and slippage, increases comfort, and offers additional sensory benefits such as impregnation of the base bead feature or zone, with a complementary lubricating, stimulating, pharmaceutically medicated, or anaesthetic fluid.

Figure 22:
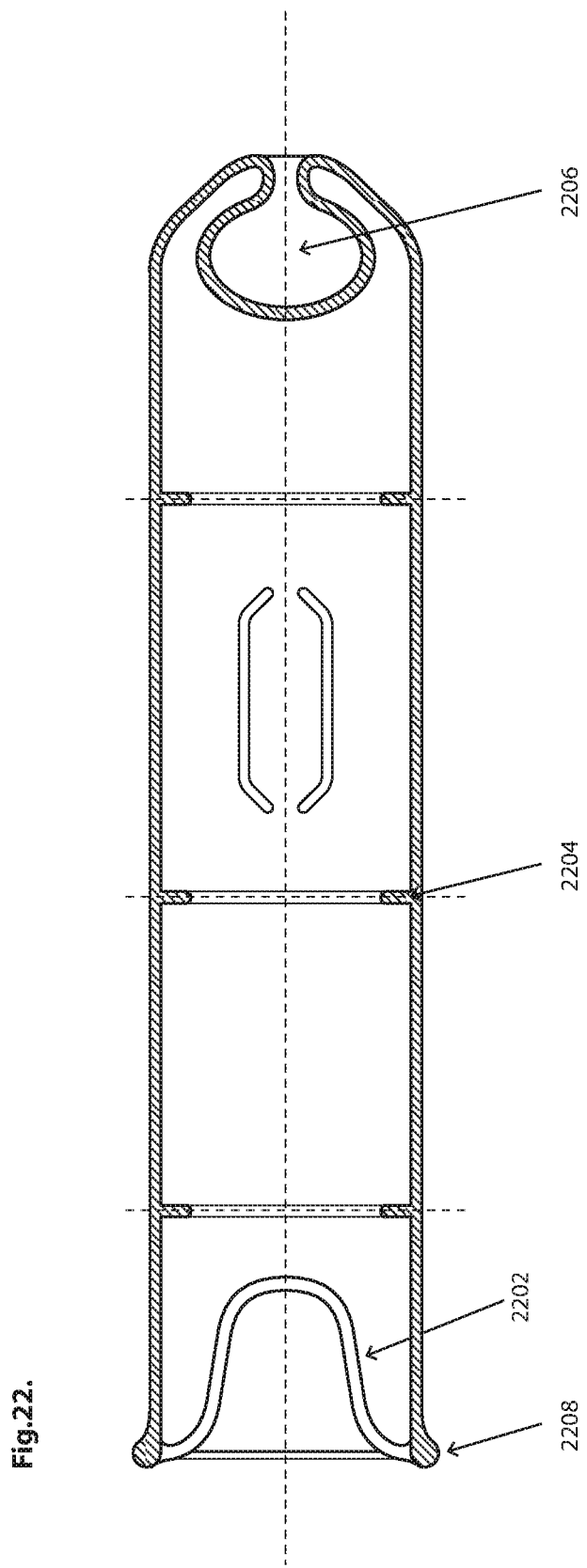
FIG. 22 provides an illustrative example of how aspects of the invention may be combined.

As the drawings illustrate, the different aspects/embodiments of the invention described above are effectively modular and may be employed in various combinations; this is particularly so for the teat variants. Thus the features described above may be implemented alone, or in combination in any one prophylactic product, and such an example combination is provided at FIG. 22. Other combinations will be apparent to those skilled in the art.

A combined advantage is a set of features intended to reduce potential for slippage and/or breakage, enhance comfort and universality of fit, and sensory benefit for users.

The features described above may be created using traditional dip and cure manufacturing or laminating, compositing, additive printing, or moulding.

No doubt many other effective alternatives will occur to the skilled person. It will be understood that the invention is not limited to the described embodiments and encompasses modifications apparent to those skilled in the art lying within the spirit and scope of the statements of invention above.

The invention claimed is:

1. A condom comprising:
   a continuous elastic tubular wall with a closed distal end and an open proximal end; and
   a teat at the closed distal end, wherein, in use, the teat is retained partially or fully inside of the continuous elastic tubular wall, and the teat forms a chamber that is fillable with a fluid or phase change formulation, wherein the chamber has an opening for externally releasing the fluid or phase change formulation in use, wherein the chamber has no fluidic communication with an interior of the condom such that in use no ejaculate can pass into the chamber;
   wherein the condom is configured to capture seminal fluid in a toroidal void around the teat during use.

2. A condom according to claim 1, wherein the continuous elastic tubular wall has at least one raised feature, each of the at least one raised feature having a portion arranged at an angle relative to a longitudinal axis of the continuous elastic tubular wall, and in use create a local force on the continuous elastic tubular wall at an angle to the longitudinal axis in response to engagement with a receiving body.

3. A condom according to claim 2, wherein the continuous elastic tubular wall has an interior surface and an exterior surface, and the at least one raised feature is formed on the interior surface, the exterior surface or both the interior surface and the exterior surface.

4. A condom according to claim 2, wherein the portion is arranged at an acute angle relative to a longitudinal axis of the continuous elastic tubular wall.

5. A condom according to claim 2, wherein the at least one raised feature is symmetric about the longitudinal axis.

6. A condom according to claim 2, wherein the at least one raised feature is symmetric about a plane transverse to the longitudinal axis.

7. A condom according to claim 2, wherein in use, in response to movement along the longitudinal axis, the at least one raised feature contracts the tubular wall between the at least one raised feature and locally expands the tubular wall outside the at least one raised feature.

8. A condom according to claim 2, wherein the at least one raised feature is non-symmetric about a plane transverse to the longitudinal axis and in use, in response to movement in a first direction along the longitudinal axis, the at least one raised feature contracts the tubular wall between the at least one raised feature and expands the tubular wall outside the at least one raised feature; and in response to movement in a second direction along the longitudinal axis, the at least one raised feature expands the tubular wall between the at least one raised feature and contracts the tubular wall outside the at least one raised feature.

9. A condom according to claim 1, wherein the teat comprises a neck and a head, and the neck of said teat is narrower than the head of said teat to retain the teat partially or fully inside of the continuous elastic tubular wall in use.

10. A condom according to claim 1, wherein at least a portion of the continuous elastic tubular wall comprising the teat or around a base of said neck of the teat is thicker than a remaining portion of the continuous elastic tubular wall to structurally retain the teat partially or fully inside of the continuous elastic tubular wall in use.

11. A condom according to claim 1, wherein the teat is prefilled with said fluid or phase change formulation during manufacture.

12. A condom according to claim 1, further comprising a frangible seal arranged to release said fluid or phase change formulation in response to movement and/or pressure immediately prior to or during use.

13. A condom according to claim 1, further comprising a user operable seal arranged to release said fluid or phase change formulation in response to manual input prior to or during use.

14. A condom according to claim 1, further comprising a seminal fluid retention feature comprising one or more internal inward protruding protrusions extending partially or completely circumferentially around the condom arranged to retain seminal fluid in the condom.

15. A condom comprising:
   a continuous elastic tubular wall with a closed distal end and an open proximal end; and
   a retaining feature towards a base of the condom, wherein the retaining feature extends circumferentially around the condom and which incorporates a stress relief feature comprising one or more loops which extend along the tubular wall for a length.

16. A condom according to claim 15, wherein the stress relief feature comprises a web enclosed by each of the one or more loops.

17. A condom according to claim 16, wherein the web comprises a bead towards the base of the condom.

18. A condom comprising:
   a continuous elastic tubular wall with a closed distal end and an open proximal end; and
   a longitudinally extended portion of thickened material at a base of the condom, wherein the longitudinally extended portion of thickened material is formed by a portion of the continuous elastic tubular wall being folded over at the open proximal end and adhered to, and/or integrated into, the tubular wall for a part of the length of the condom.

19. A condom according to claim 18, wherein the portion of the continuous elastic tubular wall folded over at the open proximal end and a remaining portion of the continuous elastic tubular wall are made of a first material.

20. A condom according to claim 18, wherein the portion of the continuous elastic tubular wall folded over at the open proximal end is made of a first material and a remaining portion of the continuous elastic tubular wall is made of a second material, wherein the first material is different to the second material.

21. A condom comprising:
   a continuous elastic tubular wall with a closed distal end and an open proximal end,
   wherein the continuous elastic tubular wall has at least one raised feature, each of the at least one raised features having a portion arranged at an angle relative to a longitudinal axis of the continuous elastic tubular wall, and in use create a local force on the continuous elastic tubular wall at an angle to the longitudinal axis to tighten a portion of the continuous elastic tubular wall in response to engagement with a receiving body,
   wherein in use, in response to movement along the longitudinal axis, the at least one raised feature contracts the tubular wall between the at least one raised feature and locally expands the tubular wall outside the at least one raised feature.

22. A condom according to claim 21, wherein the local force on the continuous elastic tubular wall at the angle to the longitudinal axis loosens a further portion of the continuous elastic tubular wall in response to engagement with the receiving body.

23. A condom comprising:
a continuous elastic tubular wall with a closed distal end and an open proximal end; and
a seminal fluid retention feature comprising one or more internal inward protruding protrusions extending partially or completely around a circumference of the condom such that a cross-section of the condom is locally reduced, the inward protruding protrusions arranged to retain seminal fluid in the condom.

* * * * *